United States Patent [19]
Belant et al.

[11] Patent Number: 5,792,468
[45] Date of Patent: Aug. 11, 1998

[54] LIME FEEDING REPELLENT

[76] Inventors: Jerrold L. Belant, 1225 State Rte. 61, Monroeville, Ohio 44847; Richard A. Dolbeer, 1228 Laguna Dr., Huron, Ohio 44839

[21] Appl. No.: 818,676

[22] Filed: Mar. 14, 1997

[51] Int. Cl.$^6$ .......................... A01N 25/12; A01N 59/06
[52] U.S. Cl. .................... 424/409; 424/405; 424/694; 424/421; 514/918
[58] Field of Search ................... 424/405, 421, 424/409, 688, 692–696

[56] References Cited

U.S. PATENT DOCUMENTS

| | | | |
|---|---|---|---|
| 901,793 | 10/1908 | Ellis | 424/421 |
| 1,511,623 | 10/1924 | McConnell | 424/421 |
| 1,629,557 | 5/1927 | Walker | 424/421 |
| 1,766,412 | 6/1930 | Taylor | 424/421 |
| 2,681,914 | 6/1954 | Gyoin | 424/421 |
| 3,024,161 | 3/1962 | McAllister | 424/421 |
| 5,300,127 | 4/1994 | Williams | 47/57.6 |
| 5,358,966 | 10/1994 | James et al. | 514/615 |
| 5,554,377 | 9/1996 | Abraham | 424/405 |

FOREIGN PATENT DOCUMENTS

| | | |
|---|---|---|
| 1601226 | 10/1981 | United Kingdom . |
| 2080669 | 2/1982 | United Kingdom . |

OTHER PUBLICATIONS

Morrison ed. Feeds & Feeding 1954 pp. 12,13 114,115.

Primary Examiner—Neil S. Levy
Attorney, Agent, or Firm—Glenna Hendricks

[57] ABSTRACT

Application of lime at a rate of 500 to 1500 kg/ha to plots desired to be protected from damage by avian and mammalian feeders has been shown to be quite effective. The lime may be administered to the plots in any form. Use of either powder or slurry form is preferred.

5 Claims, No Drawings

LIME FEEDING REPELLENT

FIELD OF THE INVENTION

This invention is related to use of lime as a feeding deterrent to bird and animal species that feed on commercially valuable seeds or plants.

BACKGROUND OF THE INVENTION

Populations of many species of wildlife that present an economic detriment have increased in recent years. For example, the number of Canada geese in the Mississippi Flyway has increased 148% (from 745,000 to 1,850,000) between 1980 and 1989. Ankney has stated that the resident population of giant Canada geese in Ontario is doubling every 5 years. Similarly, deer populations have increased dramatically in many areas. For example, the feeding of geese causes not only loss of income from crops, but also the soiling of residential, business and recreational areas. Similarly, blackbirds can cause substantial economic loss of a variety of agricultural crops. Dolber reported a 4 million to 7 million dollar annual loss of corn from blackbird damage during 1977–1979 in Ohio. In 1981, depredation by blackbirds on ripening field corn in the United States was estimated at 272,154 metric tons (a value of 31 million dollars). Although a variety of mechanical frightening and harassment devices have been employed in efforts to alleviate these conflicts, only one repellent, methyl anthranilate, is currently registered with the U.S. Environmental Protection Agency for use in addressing a few problems.

Nationwide, deer and geese cause extensive damage to orchards, tree nurseries, sprouting grain crops and other agricultural commodities. Furthermore, presence of geese or dear in the area of airports creates an unacceptable hazard to aviation.

Though populations of blackbirds have remained constant over the past 30 years, this group of birds also causes considerable economic loss. Blackbirds are responsible for 7% of wildlife strikes with U.S. civilian aircraft from 1993 to 1995.

Several studies have evaluated the efficacy of particulates as avian feeding repellents. Clays, plaster of Paris, Portland cement and gypsum-based pesticide particles coated with graphite have shown some efficacy in reducing food consumption by birds. It has also been found that food treated with activated charcoal or white quartz sand and turf treated with charcoal secured some protection from starlings and snow geese.

DETAILED DESCRIPTION OF THE INVENTION

It is the purpose of this invention to discourage wild life from feeding in both agricultural and non-agricultural locations.

In studying the problem the inventors compared the efficacy of three particulate repellents (lime, charcoal and sand) and a candidate silica-based repellant. The minimum effective concentration of the repellants (% g/g) and the effectiveness of the particulates between taxa (birds and mammals) in controlled aviary and field trials were studied.

The method of the invention comprises application of lime at a rate of 200 to 800 kg/ha to plots desired to be protected from damage by avian feeders. A rate that will be useful in most instances is 300 to 550 kg/ha. The lime may be administered to the plots in any form. Use of either powder or slurry form is preferred.

Lime may also be applied for purposes of protecting seeds from ingestion by birds. In such instances lime at the rate of 4% to 25% of the weight of the grain may be applied either as a powder or as a slurry to the grain. The lime is, for example, useful for discouraging eating of grain when the lime is applied to the seed. The seeds may be exposed either by spraying with a slurry or agitating in a lime slurry. The application of lime by slurry is particularly useful for treatment of seeds before planting. It is also possible to spray a newly seeded area with slurry to prevent ingestion of the seeds by avian feeders.

The amounts of lime used in the methods of the invention are considerably less than the amounts usually used for agricultural and horticultural purposes to raise pH of the soil.

MATERIALS AND METHODS

For all testing, dolomitic hydrated lime (hereinafter referred to simply as "lime") was purchased from GenLime Group, L.P., Genoa, Ohio., which was comprised primarily of $Ca(OH))_2MgO$ and has a pH of about 11.7. This product contained minimum concentrations of 30% Ca, 16% Mg,42% Ca oxide, and 27% Mg oxide. Particle size is variable, with 99% passing trough 20 mesh and 67% passing through 100 mesh. This lime is commonly used in turf, garden and agricultural applications.

NUTRA-LITE™ (10 to ≦60 mesh (no CAS no.) was obtained from Montana Mineral Products, Clinton, Montana) is produced from volcanic rock derived from granitic magma. NUTRA-LITE™ consists primarily of $SiO2$ (70%) and $A1203$ (13.5%). This particulate also contains lesser 5%) amounts of 11 other elements, including Fe, Mg and Ca. Preliminary observations of Canada geese on turf treated with NUTRA-LITE™ suggest this particulate may also be effective as a tactile repellent. Activated charcoal (20 to 60 mesh, CAS No. 64365-11-3) and quite quartz sand (50 to 70 mesh, CAS No. 14808-60- 7) were obtained from Sigma Chemical Company, St. Louis, Miss.

Adult male brown-headed cowbirds (mean mass=45 g) were captured in decoy traps in northern Ohio during July, 1995 and transported to an outdoor aviary in Erie County. Cowbirds were held in groups in 2.5×2.5×2.0 meter holding cages in the outdoor aviary until testing. Experimentally-naive birds were used for each test and were released after completion of the experiment.

Flightless Canada geese (mean mass=2.95 kg) of undetermined sex were captured during molt in northern Ohio during June, 1995 and transported to a 2-ha fenced pond in Erie County. Grass and shade was available along the perimeter of the pond. The primaries from 1 wing of each goose were plucked before being released into this pond facility. Cracked or whole-kernel corn was provided as a food supplement. A 0.4-ha holding area adjacent to the pond was used to separate experimental from non-experimental geese. This holding area contained grass and shade and included about 20 m2 of pond. Geese maintained this area were also provided corn. A 25 m fenced chute connected the holding area to the test site which consisted of 4 10×21 meter pens constructed of 1.5 meter high fence in a grass area. A 1 m wide buffer of grass was delineated using spray paint such that each pen consisted of 2 10×10 m plots (1 each, treatment and control). Two pans of water 0.5 m in diameter were located within each buffer area. Pens were mowed approximately every 7 days. A rain gauge was placed at the test site to monitor precipitation. Experimentally-naive geese were used for each test and were released after completion of the experiments.

CAGE TESTING

Example 1

Sixteen pairs of brown-headed cowbirds were selected randomly, banded, and placed in 1×1.5×0.5 meter cages containing water, grit and mixed bird seed. Treatment of groups of 8 birds (4 cages) was established by systematically assigning treatments. For four days immediately preceding testing, birds were provided 2 cups (0.1 L) containing millet. Each cup was attached to a pan 22 cm in diameter which collected spillage.

On day 1, cowbirds were weighed at 0900 and two food cups were placed in each cage. One cup contained 15.0 g of millet and the other 25.0 g. millet mixed with lime. Concentration of lime in the test groups were, variously, 25%, 12.5% and 6.25% lime (g/g). All other food was removed. Water and grit remained available. For the next 4 days, cups were removed at 0900 and replaced with fresh millet or millet/lime mixtures. Positions of the cups were randomized each day. The contents of removed cups, including spillage, were weighted to determine consumption. Final 24 hour consumption was adjusted for moisture gain or loss based on weight changes of control cups of millet and millet/lime placed adjacent to the cages. Cowbirds were reweighed at 0900 on day 4. A similar 1-choice test was conducted simultaneously with the 2-choice tests, except that both food cups contained 25 g millet mixed with 25% lime (g/g). Four replicates of each of the four tests were conducted.

Consumption of food was compared using a 3 factor repeated measures analysis of variance (ANOVA) (SAS Institute, Inc., 1988). Tukey tests were used to isolate differences among means. Changes in body mass of cowbirds for each test were compared using t-tests. all means were reported with+standard error.

RESULTS

Overall, brown-headed cowbirds consumed more untreated millet than treated millet. For 2-choice groups, there was a $\geq 94\%$ reduction in consumption of lime-treated millet compared to consumption of untreated millet. Total mean daily consumption of millet by cowbirds in the 1-choice group (10.49±2.63 g) was less than total mean daily consumption of millet by cowbirds in 2-choice groups ($\geq 17.70\pm6.37$ g). Total mean daily consumption was similar among the three 1-choice groups.

Consumption of millet increased overall from day 1 to day 3, then declined on day 4. The group-day iteration reflected increased consumption of millet on day 3–4 by cowbirds in the 1choice group, which equalled consumption of millet by cowbirds in the 2-choice groups.

Mean mass of cowbirds in the 1-choice group decreased 7.4% during the 4 day test. In contrast, mean body mass of cowbirds remained constant in 2-choice groups with 12.5% and 6.25% lime, respectively and increased 2.2% in the 2-choice group with 25% lime.

Example 2

Sixteen Canada geese were selected randomly from the holding area and placed individually in 2.5×2.5×2.1 meter outdoor holding cages set on a paved surface. Treatment groups of 4 birds (4 cages) were established by systematically assigning treatments to cages. Geese were provided with whole corn and water ad lib for a 4-day period prior to testing. No alternative food was available.

On day 1, geese were weighted at 0900 and two food pans (8 L) were placed in each cage. For 2-choice tests, 1 pan contained 1.0 kg whole-kernel corn and the other 1.0 kg corn mixed with 25%, 12.5% and 6.25% lime (g/g). For the one-choice test, each food tray contained 1.0 kg of corn mixed with 25% lime (g/g). All other food was removed. Water remained available at all times. The analysis was performed as in Example 1.

RESULTS

Canada geese consumed more untreated corn than treated corn. For 2-choice groups, there was a $\geq 89\%$ reduction in consumption of lime-treated corn compared to consumption of untreated corn. Total mean daily consumption of corn by geese in the 1-choice group was less (18.8±18.3 g) than total mean daily consumption of corn by geese in 2-choice groups ($\geq 87.0\pm30.1$ g). Total mean consumption was similar among the three 2-choice groups.

Consumption of corn increased overall from day 1 to day 3, then declined on day 4. There was no interaction of day with treatment or test group. There was a 3-way interaction of day, treatment and test group, primarily as a consequence of geese eating no treated corn in the 1-choice test on day 2.

Mean body mass of geese in the 1-choice group decreased 4.1% during the 4-day test. In contrast, mean body mass of geese remained constant during the test in the three 2-choice groups.

TURF TESTING

Example 3

For 7 consecutive days, 24 geese were herded from the holding area to the pan test site. Six geese were placed in each pen at 0900 and allowed to graze until 1600, when they were herded back to the holding area. Numbered neck bands were attached to each goose to ensure the same individuals were placed in the same pens each day.

On the day prior to testing, grass in the pens was mowed and 1 plot in each pen was selected randomly and treated with lime using a push-operated rotary spreader to spread lime at a rate of 544 kg/ha. To ensure even coverage, the spreader was operated in two series of perpendicular transects over each entire plot. Grass in treated plots was gray-white in color. Remaining plots served as controls.

Two individuals positioned in separate vehicles 10–15 m from the pens monitored goose activity. Vehicles had been positioned near the pens frequently during pretreatment to ensure their presence did not modify goose behavior. Observations occurred daily for 60 minutes, beginning immediately after geese were released into the pens. Each observer watched geese in 2 pens, alternating observations between pens every 60 seconds for a daily total of 30 minutes of observation per pen. During each 60 second interval, observers recorded the total number of bill contacts with grass in each plot. Mean numbers of bill contacts on each plot were determined and compared between treatments using randomized block (pens) ANOVA with repeated measures. All means were reported with±standard error.

RESULTS

It was determined that the number of bill contacts with grass on lime-treated plots was less than the number on control plots on days 1–3. There were no differences in bill contacts on treated and control plots after day 3. There was a day effect for bill contacts, with overall increase in number of contacts observed on day 7.

On several occasions geese were observed to drink water or shake their heads laterally after a series of bill contacts with lime-treated grass. These behaviors were not observed in geese feeding on control plots.

There was no rain the first three days of the study. The rain fall was 0.1, 2, 15.5, and 1 mm on days 4–7, respectively. Lime remained visible on treated plots ≧7 days posttreatment. The grass showed no signs of phytotoxicity through 20 days observation posttreatment.

Example 4

Experimentally-naive geese were herded into pens 40 days after the conclusion of Example 3. The methodology was the same as in Example 3 except that the lime was sprayed in the form of a slurry with application rate of 544 kg/ha. The slurry was a 1:20 (g/g) lime/water mixture with 0.001% (v/v) binding agent (EXHALT 800, obtained from Pbi/Gordon Corporation, Kansas City, Kans.)

RESULTS

More bill contacts were observed on control plots (21.3±2.2) than on treated plots (9.7±1.4) overall. There were no differences on days 1 and 4–7. There was also a day effect for bill contacts, with increased numbers of bill contacts observed overall on days 1–2 and 4. The drinking and head-shaking was observed in geese eating from lime-treated grass.

Example 5

Rice was mixed with EXHALT, then with dry lime (4% g/g). The rice was then placed in a water bath containing 4% lime for 24 hours. The treated rice was then spread on three randomly assigned plots beside three other randomly assigned plots on which untreated rice had been spread. The rice which was exposed to lime was rejected by cowbirds in a 2-choice study in favor of rice which had not been exposed to lime slurry.

Example 6

Comparative studies were done using charcoal, Nutra-lite or sand which were mechanically mixed with millet to achieve concentrations 1%, 2% and 4% (g/g) repellent. Corn oil (10 ml/kg) was used to cause repellents to adhere to the millet. Untreated millet was mixed similarly with an equivalent amount of corn oil only as a control.

Twelve birds were selected at random, and housed individually in cages measuring 1×1.5×0.5 meters containing water and millet. For 3 days immediately preceding the study, birds were provided 1 cup (0.1 L) containing millet. Each cup was attached to a pan 24 cm in diameter to catch spillage.

On day 1 of the 4-day study, cowbirds were weighed at 0900 hr and 2 food cups were placed in each cage. One cup contained 20 g of millet/corn oil mixture and the other 20.0 g millet/corn containing one of 1%, 2% or 4% repellent. Treatments were assigned systematically to cages such that 4 replicates of each repellent and concentration occurred. Positions of cups in each cage were randomized. Cups were removed the following day at 0900 hours. The contents of removed cups, including spillage, were weighed to determine consumption. Twenty four hour consumption was adjusted for moisture gain or loss based on weight changes of control cups of millet and millet/repellent placed adjacent to cages. This procedure was repeated daily through day 4. The cowbirds were reweighed at 0900 hr. on day 4.

The change (decrease) in consumption of treated millet versus untreated millet for two-choice (treated/untreated) was:

Lime: >99% less of lime-treated (4%) eaten
Charcoal: >53% less of charcoal treated eaten
Nutra-lite: >78% less of NUTRA-LITE™ treated eaten Example 7

The effect of lime as a repellent to prevent white-tailed deer from feeding was studied. Treated corn was prepared in 31.8-kg batches using a cement mixer. Corn was tumbled dry for 1 minute before adding corn oil (10 ml/kg corn) and a repellent (4% g/g) and mixed for 3 additional minutes. Untreated corn was mixed similarly but without a repellent. The studies were conducted during August, 1996 at a 2,200-ha site. During December, 1995, this area was estimated to have a minimum white-tail deer population of 825 (≧38/km2).

Eight feeding stations were established located ≧1 km apart using whole-kernel corn placed in 1 adjacent long cattle feed troughs 1.2 m long. A high plastic fence (1.5 m) was erected on 3 sides of an area 5×5 m. The feed troughs were located inside the fenced areas about 1 m from the back. To monitor corn consumption, feed troughs were calibrated using wood stakes that were marked to measure corn at 4.6 kg intervals. A calibrated wood stake was positioned at each end of each trough. Thus, corn consumption was estimated to the nearest 2.3 kg. Corn was added to feed troughs as necessary to maintain a constant food supply and the amount of corn consumed was recorded.

To condition deer to use feeding stations, we monitored each station 3 to 4 times/week for about 1 month prior to the study. The study consisted of 1 4-day, 2-choice trials. For the first trial, 4 sites were selected at random to receive The corn treated with lime, charcoal or NUTRA-LITE™ was consumed less than was the untreated corn. The mean daily percentage reduction in consumption was as follows:

Lime: decrease of 87%
Charcoal: decrease of 71%
NUTRA-LITE™: decrease of about 45%

DISCUSSION

The data indicates that the geese were more affected by the lime powder than by the slurry on day one. A possible explanation is that the powder is more likely concentrated at the upper portion of turf, whereas the lime slurry was more evenly distributed vertically within the grass. Hence, geese may have ingested more lime per bill contact when first exposed to the plot treated with powdered lime. It is also possible that particles of powdered lime may have been inhaled during grazing, causing nasal irritation and increasing repellency.

Phytotoxic effect on grass was not observed during this study ≧40 days posttreatment using application rates of 544 kg/ha. Thus, it is expected that agricultural crops and turf (most particularly, monocots) would probably not be damaged at ≦800 kg/ha. The application of lime on fields to increase pH of overly acid soil is about 4500 kg/ha, though it may be as low as 1500 kg/ha if applied on a yearly basis. Hence, the amounts needed to discourage geese from feeding should not be expected to damage most grass.

Using the amounts of lime and the methods disclosed herein, it is believed that administration of lime at the rate of 500 to 1500 kg/ha would greatly decrease the number of unwanted avian feeders. The methods disclosed herein would be particularly useful in discouraging feeding by migratory birds, since relatively heavy application of lime over a short period of time would greatly reduce damage to crops and to recreational areas.

The use of lime to protect growing crops from damage may be accomplished by application of lime at 1-week intervals to sprouting crops such as corn and soybeans.

Lime might also be applied to landfills to reduce feeding by birds on exposed refuse.

We claim:

1. A method of discouraging undesired avian species from feeding on specific plots consisting essentially of application of lime at a rate of 500 to 1500 kg/ha to said plots.

2. A method of claim 1 wherein the amount administered is 300 to 550 kg/ha.

3. A method of claim 1 wherein the lime is applied as a slurry.

4. A method of claim 1 wherein the lime is applied as a powder.

5. A method of claim 1 wherein the lime is applied by spraying a slurry on a seeded field.

* * * * *